United States Patent [19]

Bernstein et al.

[11] 4,024,401
[45] May 17, 1977

[54] X-RAY APPARATUS

[75] Inventors: Stanley Bernstein, Whitefish Bay;
Thomas W. Lambert, Hales Corners;
Philip J. Griswa, Waukesha; Lucius Stagg, Milwaukee, all of Wis.

[73] Assignee: General Electric Company, Schenectady, N.Y.

[22] Filed: June 4, 1976

[21] Appl. No.: 692,866

Related U.S. Application Data

[63] Continuation of Ser. No. 632,235, Nov. 17, 1975, abandoned.

[52] U.S. Cl. .................... 250/439 R; 250/445 R; 250/490; 250/523
[51] Int. Cl.² .................................. G03D 41/16
[58] Field of Search .......... 250/439 R, 444, 445 R, 250/445 T, 446, 447, 448, 449, 490, 521, 522, 523, 524, 525

[56] References Cited

UNITED STATES PATENTS

| | | | |
|---|---|---|---|
| 3,121,167 | 2/1964 | Latson | 250/523 |
| 3,784,837 | 1/1974 | Holmstrom | 250/523 |
| 3,838,286 | 9/1974 | Prendergast | 250/445 T |

*Primary Examiner*—Craig E. Church
*Attorney, Agent, or Firm*—Ralph G. Hohenfeldt

[57] ABSTRACT

X-ray apparatus includes a floor mounted enclosure, a patient supporting table on the enclosure, an X-ray tube casing mounted for angulating in the enclosure, X-ray imaging devices unitarily supported for angulating on a cantilever arm located above the table, and an extensible and contractible and optionally removable link arm for coupling the tube casing and image devices, respectively, to enable their coordinate longitudinal angulation or selectively to enable maintaining the X-ray tube and imaging devices in a fixed vertical relationship.

16 Claims, 5 Drawing Figures

X-RAY APPARATUS

This is a continuation, of application Ser. No. 632,235, filed Nov. 17, 1975, now abandoned.

BACKGROUND OF THE INVENTION

This invention relates to apparatus which can be used for general X-ray diagnostic purposes and features the capability for being quickly converted to a specialized apparatus for making arteriographic studies of the heart.

Some prior apparatus for performing these specialized cardiac procedures have an X-ray source arranged on one side of a patient supporting table and an X-ray imaging system on the other side with the source and imaging system on a mounting which enables the central X-ray beam to remain directed at the image plane for various angles at which viewing of the heart is desired. In some prior designs the patient is supported for limited lengthwise turning and longitudinal angulation relative to the X-ray beam to provide for viewing the heart at the various angles. In other designs, the X-ray source can be angulated while the patient is supported for limited lengthwise rotation or no rotation at all.

In known types of apparatus that is dedicated to making arteriographic studies the patient is supported on an X-ray transmissive tabletop which overhangs or extends in cantilever fashion from a base. The X-ray source and imaging devices are supported on the ends of the two sides of a U-shaped arm assembly to dispose them on opposite sides of the upper part of the body which rests on the cantilever tabletop. The curved base of the U-shaped arm assembly, which connects the nominally horizontal sides, is mounted for sliding in a curved path in a bearing structure or guide that is supported on a horizontal shaft. The shaft may be journalled in a floor mounted support structure. The apparatus is arranged so the normally horizontally extending sides of the U-shaped assembly project lengthwise of the patient and tabletop in the cranial to caudal direction.

In another prior art apparatus that is dedicated to making heart examinations, a C-shaped arm is carried on a floor mounted or ceiling mounted stand. The C-arm has an X-ray source mounted on one terminus and an imaging assembly mounted on the other. The arrangement is such that the arm may be passed laterally over a patient suspended in cantilever fashion on a tabletop. This arrangement permits lateral and longitudinal angulation of the source and imaging devices such that the heart may be viewed from various angles.

A significant problem with both types of apparatus discussed above is that the X-ray source and imaging device are both located in free space such that the cardioradiologist, attendants and patient are exposed to stray radiation and radiation that is scattered from the imaging device and the structural elements around it. Since the source and imaging device in conjunction with the arm must be free to move at all angles around the patient, it is not possible to totally enclose either of them to minimize stray and scattered radiation.

Another problem with mounting an X-ray source and imaging device on a U-arm or C-arm is that it is difficult to provide for angulating the X-ray source longitudinally of the patient coordinately with the imaging device. Also, since the arm approaches the patient from the head end when a U-arm is used and from the side at the head end when a C-arm is used, and there is usually a floor mounted support for the arm, the apparatus necessarily requires much space in a cardiovascular examination room. This is obviously undesirable.

Another disadvantage of some prior art heart examination systems is that when the unitarily mounted X-ray source and image device are maneuvered to the desired viewing angle there is a chance that the patient may be struck by the equipment.

Another disadvantage of the prior apparatus discussed above in that it must be made very massive to obtain the rigidity required for maintaining the X-ray beam in unswerving vibration-free alignment with the image plane. This is especially true where the X-ray source and image device are on the ends of long parallel arms. Massiveness also requires more manual or mechanical force to position the apparatus relative to a patient. The problem is aggravated by the need for the imaging system to include an image amplifier, a television camera, a spot film camera and a cine camera which have substantial total weight.

Despite the continuing redevelopment and refinement of cardiovascular and arteriographic X-ray apparatus, procedures for getting views of the entire coronary arterial system is still inconvenient and painstaking with prior apparatus.

SUMMARY OF THE INVENTION

A general object of this invention is to eliminate or mitigate the aforementioned disadvantages and restraints of prior art arteriographic X-ray apparatus.

Another object is to provide X-ray apparatus that can be used for general radiological examinations but which may be converted quickly and with little effort to a system which has the desirable attributes of one that is specialized or dedicated to coronary arteriography.

A further object is to provide apparatus that permits longitudinal angulation of the X-ray source and imaging device along the sagittal plane of the patient a sufficient extent to permit viewing of the heart with minimum superposition of the blood vessels and tissue of interest.

Other objects are to provide arteriographic apparatus which: is rigid and stable but has minimum mass; is versatile insofar as procedures and use of auxiliary equipment are concerned; is constructed and arranged for cooperation with bi-plane apparatus to facilitate ventriculographic procedures; and, is easy to use.

Another object is to provide apparatus which has the X-ray source in a radiation impermeable enclosure where there is a close coupling between the source, the patient support and the patient such that stray and scattered radiation in the room is reduced.

Still other objects are to provide heart examination X-ray apparatus that occupies little floor space, that is convenient to work around, that affords maximum patient comfort and facile handling of the patient during the examination and when placing and removing the patient relative to the examination table.

An important object of the invention is to provide X-ray arteriographic examination apparatus wherein the imaging device is mounted on a vertically movable cantilever arm which affords access to as many as three sides on the image amplifier for attaching a variety of viewing and recording devices such as a television camera, a spot film camera and a cine camera.

How the aforementioned objects and other more specific objects of the invention are achieved will now be set forth in a more detailed description of an illustrative embodiment of the invention in conjunction with the drawings.

DESCRIPTION OF A PREFERRED EMBODIMENT

Figure 1:
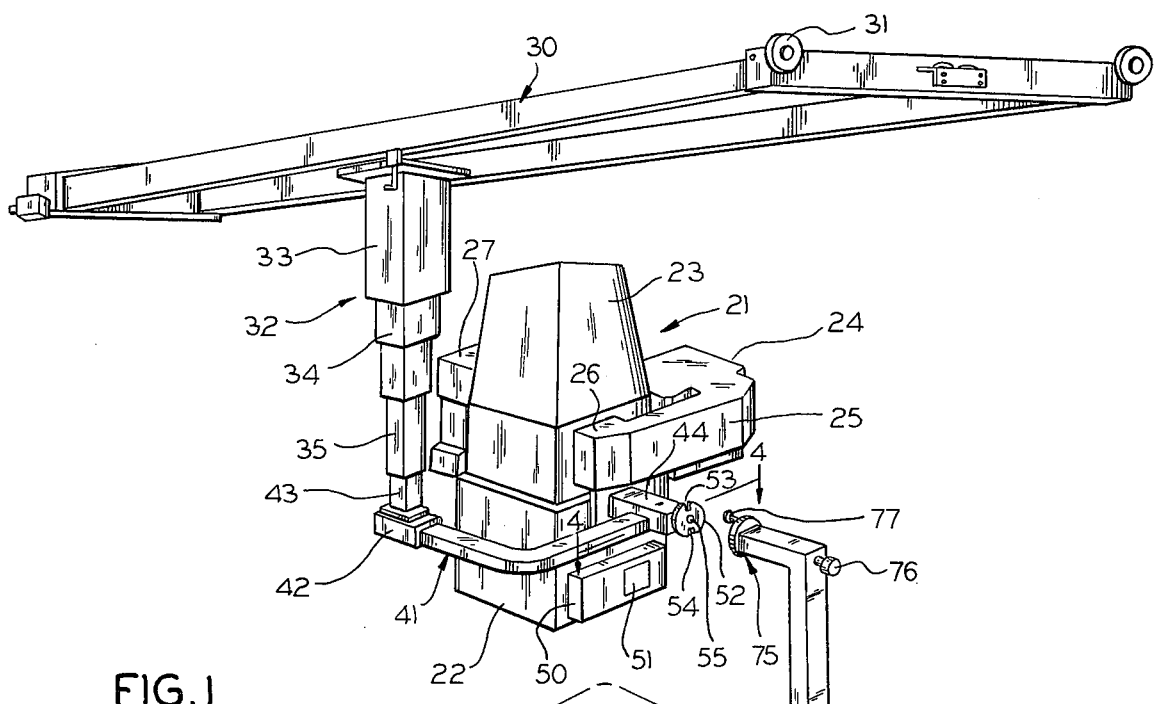
FIG. 1 shows the general arrangement of the parts of the new X-ray table with the link arm for converting it to a specialized coronary arteriographic table, said link arm being shown disconnected, the base structure being shown in phantom and the patient supporting tabletop being omitted.
Figure 2:
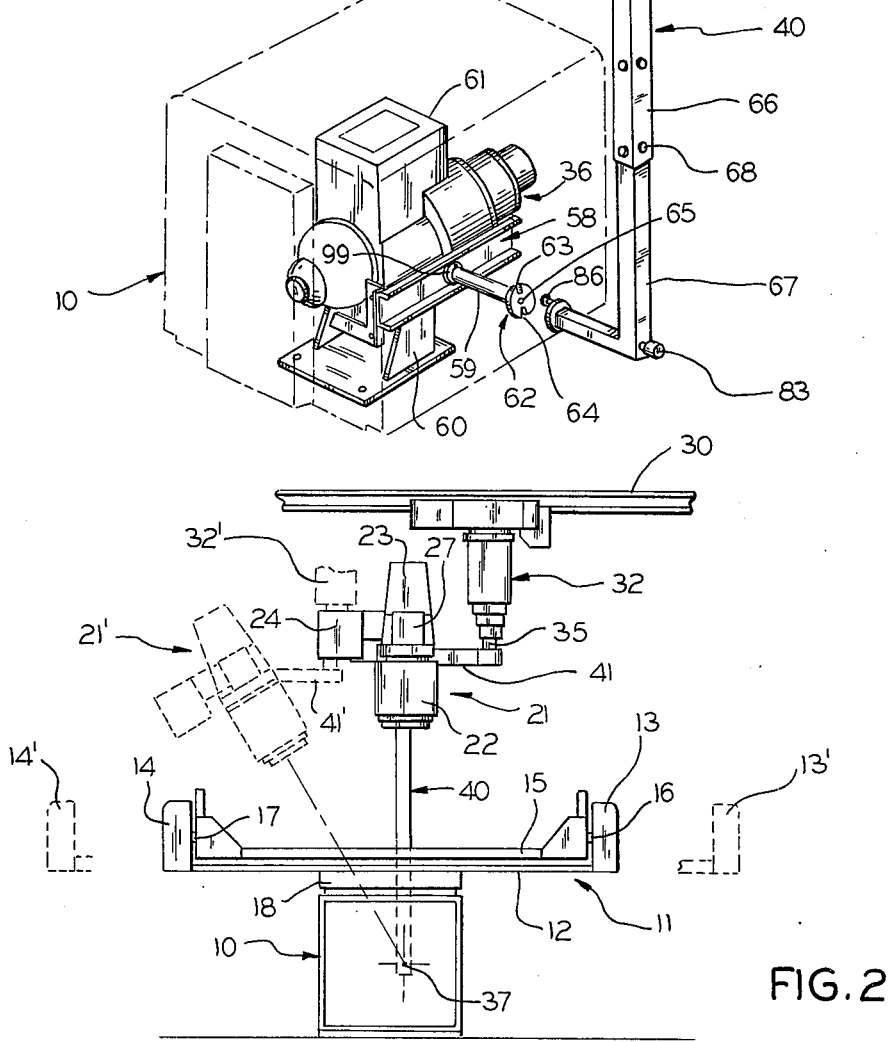
FIG. 2 shows a front elevation of the table where the X-ray image intensifier assembly is shown in solid lines in its central position over the table and wherein the intensifier is shown in phantom lines in an illustrative angulated position.

FIGS. 1 and 2 illustrate that the table assembly comprises a base or housing 10 which is shown in phantom in FIG. 1 and solid lines in FIG. 2. The housing is impermeable to X-rays except for an opening in its upper region which is covered by an X-ray permeable patient support or table 11 as may be seen in FIG. 2. The patient support has an X-ray permeable generally planar base 12 and opposed upstanding end columns 13 and 14. A cradle 15 is mounted in the columns and is adapted for rotating the patient about a longitudinal axis, that is, about an axis that parallels the plane of the paper in FIG. 2. The shafts on which cradle 15 is mounted for rotation about a longitudinal axis are marked 16 and 17.

Table base 12 is mounted on a support 18 which contains mechanism, not shown, to facilitate shifting the base longitudinally in either direction as suggested by the phantom representation of the upstanding end columns 13' and 14'. Table base 12 is also shiftable laterally, that is, toward and away from an observer in FIG. 2. The cradle structure just described and the provision for shifting the patient longitudinally and laterally with respect to an X-ray source are known features in X-ray apparatus.

Mounted above the X-ray table is an image intensifier system generally designated by the reference numeral 21. The intensifier comprise a housing which has a lower part marked 22 and an upper part marked 23. The lower part contains an electronic image amplifying tube, not visible, but which is a well known type that converts an X-ray image into a small bright optical image that appears on a phosphorescent disk. The upper part 23 of the intensifier system contains a television camera, not visible, which is used to permit display of the converted X-ray image on a television monitor. The term "image intensifier assembly" is used herein for convenience and brevity to designate the assembly of the image intensifier tube, its housing and devices that may be contained in or affiliated therewith for distributing and recording the image.

The manner in which the image intensifier system 21 is mounted in accordance with the invention permits visualizing or recording the image in at least three ways. The first way, namely, with a television camera has been described already. Another way is with a spot film camera 24 which is mounted on image intensifier assembly 21. The output image of the image intensifier is directed through a light tunnel 25 in which there is mirror system, not visible, which has an image inlet end 26 and an outlet that leads to camera 24. A spot film or still camera of the type here under consideration may provide a photographic film about 105 mm square but other sizes are some times used.

Image intensifier assembly 21 has another port at its front for providing an image to a cine recording camera 27. Generally, cine cameras used for recording optical versions of diagnostic X-ray image use 3 mm film and run at a much higher rate than ordinary cine cameras and they stop abruptly so as to cause vibrations which are minimized with the new intensifier mounting.

In the commercial embodiment of the design herein described, the optical systems for recording camera 24, cine camera 27 and the television camera within intensifier assembly 21 are arranged so that the image displayed on the television monitor in real time has the same orientation as the images recorded on film.

To facilitate using the system in the coronary arteriographic and general purpose modes, the image intensifier system 21 is mounted for being angulated longitudinally and for being raised and lowered and for executing combinations of these motions relative to a patient that is supported on table 11.

There are support means for the image intensifier assembly 21 which enables the assembly to angulate about a laterally directed axis, to be raised and lowered and to be translated longitudinally as can be seen in FIG. 1. In this embodiment the support means comprises a crane 30 which is movable near the ceiling of the room in the longitudinal direction of the table. The crane has wheels 31, which run on stationary overhead tracks, not shown. Mounted to crane 30 is a telescoping arm assembly 32 comprised of a fixed section 33 and several vertically movable telescoping sections such as 34 and 35. The counterpoising system for the telescoping arm assembly 32 is not shown and need not be discussed since a variety of counterpoising systems are known to those skilled in the art. In some installations the telescoping arm 32 has its upper section 33 provided with wheels that enable the arm to be traversed in the lateral direction, that is, lengthwise of crane 30. This permits the telescoping arm 32 and the image intensifier system 21 to be parked at the side of the room away from the table. Provision for lateral movement of the telescoping arm is optional. However, provision for longitudinal shifting of the intensifier assembly by the means just described or by other suitable means is essential to operating the nex X-ray system in its arteriographic mode.

In accordance with the invention, the image intensifier system 21 is adapted for angulation coordinately or synchronously with an X-ray tube which is inside of a casing 36 that is located within the floor mounted housing 10 which supports the patient table 11. Synchronous angulation of the image intensifier assembly 21 and X-ray tube casing 36 results in the central X-ray beam emanating from the focal spot of the X-ray tube remaining substantially centered on and perpendicular to the input image plane of the image intensifier. The location of the X-ray tube focal spot is marked 37 in FIG. 2. In this embodiment, the X-ray tube casing 36 and intensifier assembly 21 are adapted to angulate jointly about 15° in one longitudinal angular direction and 30° in the other. Greater and, possibly, somewhat lesser angles may be permissible but it has been found that with the angular range of 45° used in this case arteriographers are able to get satisfactory angular and perpendicular views of coronary blood vessels which, with conventional methods might be concealed or have other blood vessels superimposed on them. The capability of the apparatus for jointly angulating the X-ray source and image intensifier system and for rotating the patient longitudinally permits placing any of the multi-directional coronary arteries perpendicular to the X-ray beam for recording. The details of the structure for mounting the X-ray tube so it may angulate will be described later in reference to FIG. 5. Joint angulation of image intensifier assembly 21 is effected with a telescoping link arm assembly 40 which will also be described in detail subsequently.

Figure 4:
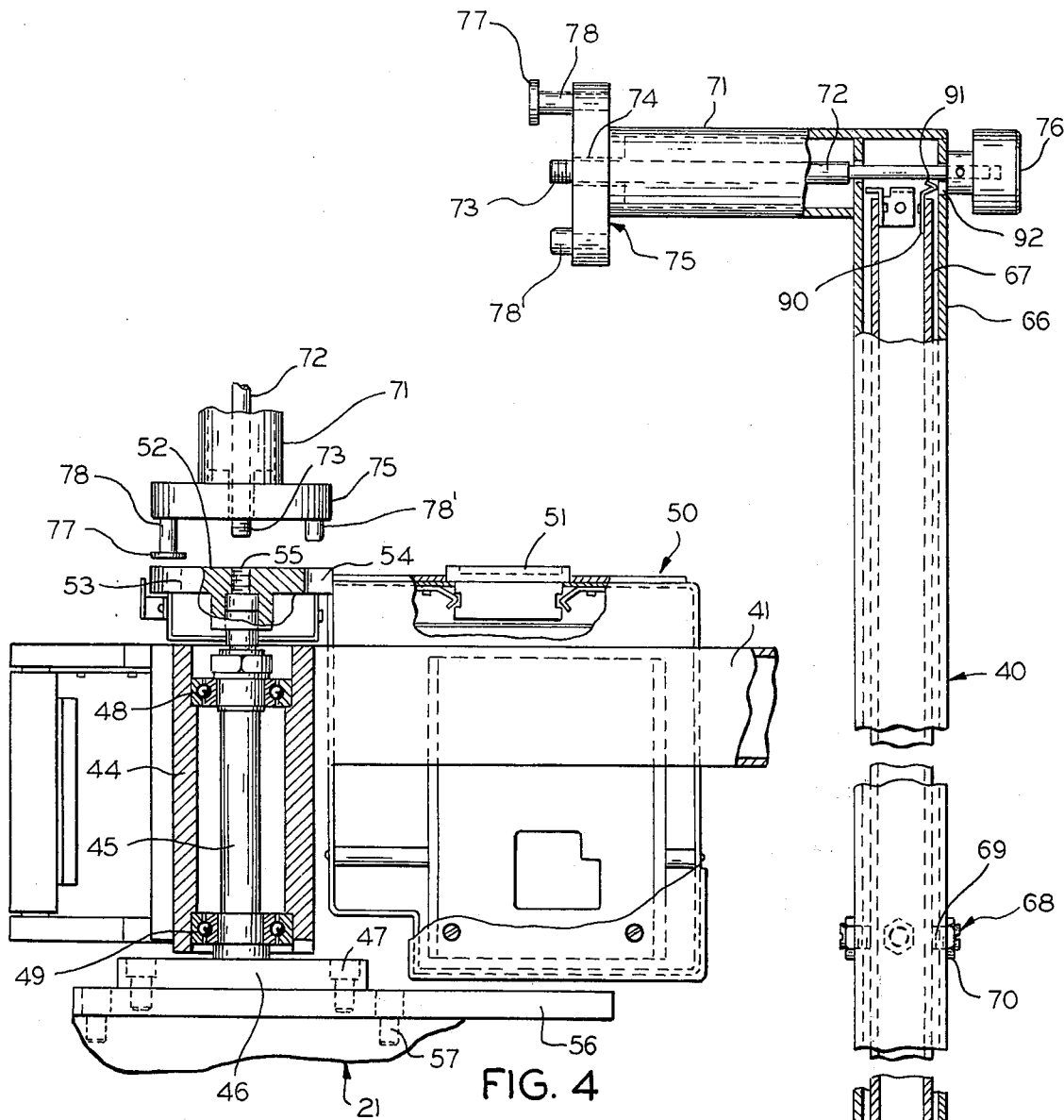
FIG. 4 is a partial horizontal section taken generally along the plane 4—4 in FIG. 1.

Attention is now invited to the new horizontally extending arm means for supporting the image receiving, intensifying and distributing assembly 21. Assembly 21 is supported in cantilever fashion on a substantially L-shaped arm means 41 which is preferably hollow. Arm 41 has an integral box-like portion 42 at one end from which a vertical post 43 extends. It will be understood that the post fits into vertically telescoping section 35 and that it is fastened therein under all circumstances. Arm 41 has another integral box-like portion 44 at its other end. A fragment of the arm 41 and a section of the box-like portion 44 can be seen in FIG. 4. The box 44 contains a shaft 45 that has a flange 46 which is fastened to a locking plate 56 by means of several screws 47. The image intensifier assembly 21, a fragment of which is shown in FIG. 4, is secured on the locking plate 56 by means of several screws such as 57. Shaft 45 is mounted in a pair of ball bearings 48 and 49 which have their outer races fixed in the box-like portion 44 which is integral with arm 41. Thus, image intensifier assembly 21 is supported in cantilever fashion on arm 41 and is mounted for bidirectional angulation about the laterally directed axis of shaft 45.

When the link arm 40, which connects image intensifier assembly 21 to the X-ray tube casing 36 is engaged, the image intensifier assembly is prevented from inadvertent angulation. When link arm 40 is disconnected, however, the image intensifier assembly 21 would be subject to swinging freely on shaft 45. Means are provided for locking the intensifier assembly 21 in a true vertical position, when the apparatus is being operated in the vertical radiography mode, so as to prohibit inadvertent rocking and to maintain the central X-ray beam in alignment with the center of the image intensifier. Means, not shown, are also provided for locking the X-ray tube against angulating in this mode. Such means can be devised readily by those skilled in the art so they need not be discussed further. There is a box 50 mounted immediately under arm 41 on the image intensifier 21 and this box has a window 51 on which legends are displayed that indicate when assembly 21 is vertical and locked such that removal of link arm 40 is permissible for the conventional vertical mode.

Referring further to FIGS. 4 and 1, it will be noted that flange 52 which is fastened to shaft 45 has two radially extending slots 53 and 54 in its periphery. The flange also has a central threaded hole 55. Slots 53 and 54 are used for coupling image intensifier assembly 21 to the X-ray tube casing 36 with link arm 40 for joint angulation as will be described shortly after the way in which the X-ray tube casing 36 is mounted has been described.

The way in which the X-ray tube casing 36 is mounted for longitudinal angulation will be discussed in reference to FIGS. 1 and 5. In FIG. 1 it is apparent that casing 36 is mounted in a cradle 58 which is journalled on a stationary base 60. The cradle 58 angulates about a laterally directed axis which is coincident with the axis of an extension shaft 59 that is fastened to the back of the cradle with a flange 99. When torque is applied to extension shaft 59 by means of link arm 40, the tube casing 36 will angulate.

Figure 5:
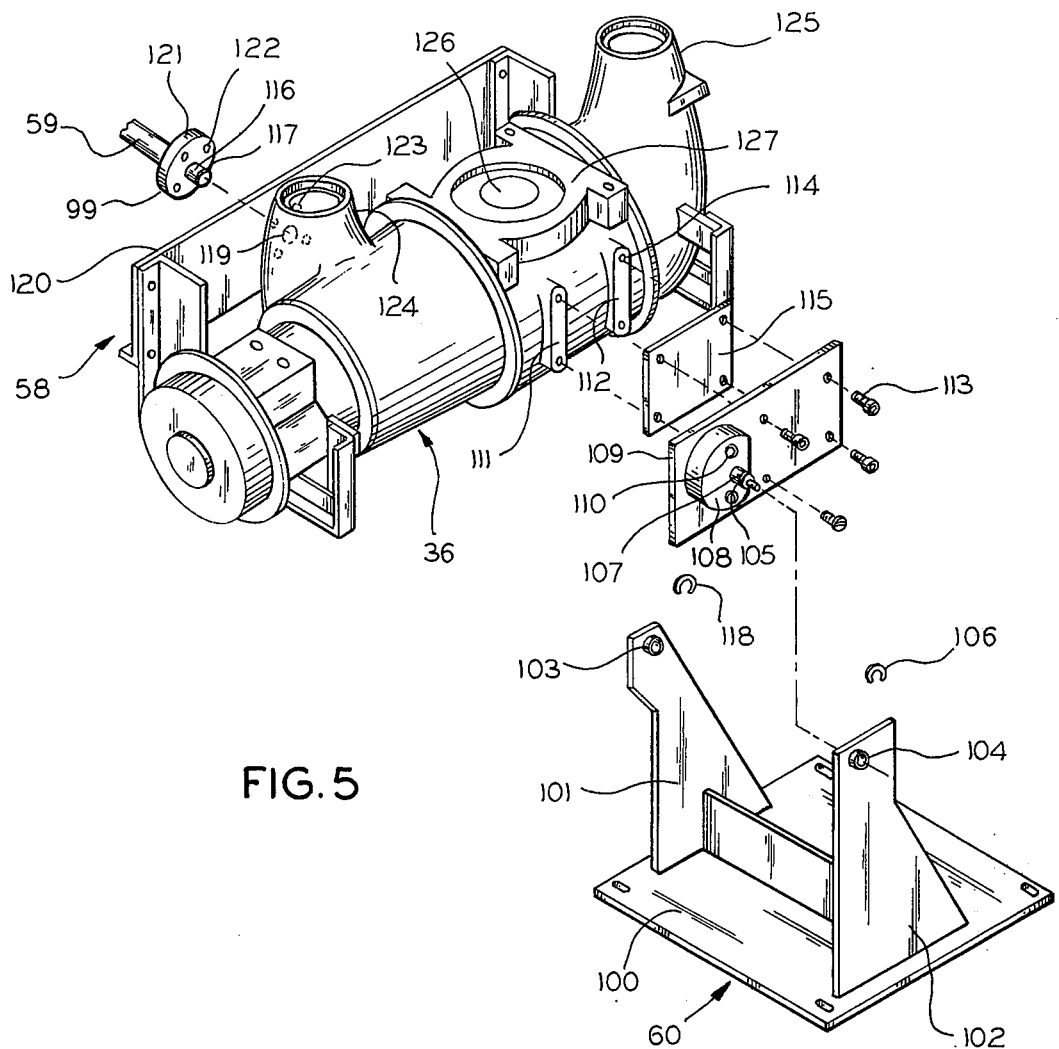
FIG. 5 is an exploded view of the X-ray tube, its cradle and its mounting base.

Now refer to FIG. 5 for a more detailed description of the mounting for the X-ray tube casing 36. Stationary base 60 has a bottom plate 100 on which a pair of upstanding columns 101 and 102 are welded. The columns have coaxial bushings 103 and 104, respectively. When the exploded view is assembled as suggested by the dashed center lines, a stub shaft 105 is journalled in bushing 104. The shaft is inhibited against axial movement with a snap ring 106 that fits into an annular groove 107 in shaft 105. The shaft 105 is on a spacer boss 108 which is held to a plate 109 with machine screws 110 which have their heads recessed. Plate 109 is mounted to a pair of bosses 111 and 112 on X-ray tube casing 36 with several screws such as 113 which enter threaded holes such as 114 in the casing. A spacer plate 115 is interposed between plate 109 and the tube casing 36.

At the rear of cradle 58 is another stub shaft 116 which has a snap ring receiving groove 117. This shaft extends through bushing 103 in base column 101 and is retained with a snap ring 118. Shaft 116 extends inwardly through a hole 119 in the rear plate 120. The shaft is on a flange 121 which is fastened to fragmentarily shown shaft 59 by means of which torque is applied to the cradle 58. Flange 121 is secured to rear plate 120 of cradle 58 by means of bolts, not shown, which extend through the several holes such as 122 and mating holes 123 in plate 120.

For the sake of completeness it is pointed out that casing 36 which contains the X-ray tube, not visible, has a pair of sockets 124 and 125 for receiving high voltage cable connectors, not shown. The X-ray beam emerges upwardly through a window opening 126 in the top of the casing. The adjacent bosses 127 are for fastening the collimator 61 which was mentioned earlier in connection with FIG. 1.

It should be noted that extension shaft 59, extending from the tube casing cradle 58 to the rear of enclosure 10 in FIG. 1 has a flange 62 fastened to it. The flange has diametrically opposite radially extending slots 63 and 64 in its periphery. Flange 62 is for coupling the X-ray tube casing cradle 58 to link arm 40. Enclosure 10, of course, has a suitable opening in its rear to permit access to flange 62 and the opening is provided with suitable shielding, not shown, for preventing emergence of radiation. Flange 62 also has a central threaded hole 65 which is used for locking the link arm 40 to it as will be described.

Figure 3:
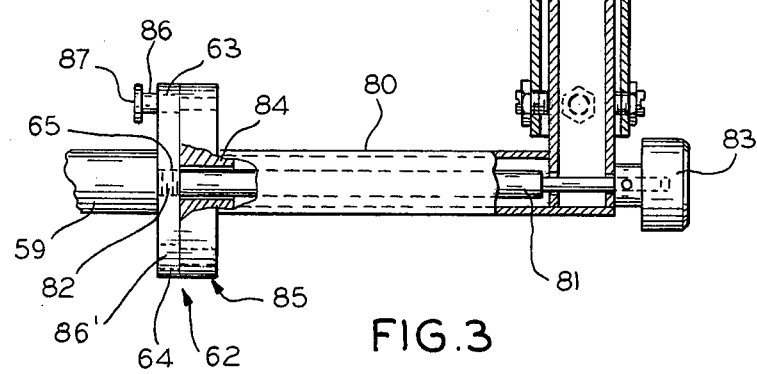
FIG. 3 is a more detailed view of the link arm illustrated in FIG. 1 with parts shown in section and other parts shown fragmentarily.

The details of the link arm 40 may be seen in FIG. 3. It comprises an outer tubular portion 66 and an inner tubular portion 67 which telescope or slide relative to each other such that the arm 40 may be extended and contracted in accordance with operating requirements. In this embodiment, the inner tube 67 is maintained in alignment with the outer tube and in low friction relationship by means of several bearing elements such as the one marked 68. These elements are essentially externally threaded plugs which thread into suitable internally threaded holes in outer tube 66 and whose end faces 69 bear on the outer surfaces of inner tube 67. The plugs each have lock nuts 70 for securing them after tubular elements 66 and 67 have been properly aligned and adjusted for minimum friction without free play. The outer ends of the plugs have a screw driver slot for facilitating their adjustment. The plugs may be any good anti-friction material such as that known by the trademark Delrin.

A laterally extending hollow section 71 is joined with the upper end of outer tube 66. A rod 72 extends through hollow section 71. Rod 72 has a thread 73 at one end. The threaded end of the rod passes freely through a central hole 74 in a flange 75 that is rigidly fastened to lateral extension 71. At its outer end, rod 72 has a manually engageable knob 76 for turning it. A pin comprised of a head 77 and a shouldered shank 78 is fixed in flange 75. The exposed part of shank 78 is sized to fit freely into radially open slot 53 in flange 52 which is fastened to shaft 45 on which the image intensifier assembly angulates. Head 77 of the pin retains link arm 40 temporarily during its installation or removal even though the lower end of the link arm is not yet coupled with X-ray tube angulating shaft 59. Flange 75 on the link arm in FIG. 3 also has a guide pin 78', which has a chamfered exposed end, projecting from it. The guide pin 78' is sized to fit into slot 54 in flange 52 so that a positive torque coupling is effected by the two pins 78 and 78' when the flange 52 on the intensifier shaft and flange 75 of the link arm are clamped together.

A laterally extending tubular member 80 is joined with the lower end of inner telescoping member 67 of the link arm. It is basically the same as the upper lateral extension 71. It is provided with a rod 81 which has a threaded end 82 at one end and a knob 83 at the other end for turning the rod. Rod 81 fits through a clearance hole 84 in a flange 85 which is rigidly attached to laterally extending tubular portion 80. A pin having a shank 86 and a head 87 is fastened in flange 85. Shank 86 is sized to fit freely into radially open slot 63 in flange 62 which is shown fragmentarily in FIG. 3 and which is the drive shaft for angulating the X-ray tube casing cradle 58. It should be noted that shank 87 in the upper flange of the link arm is longer than shank 86 in the lower flange 85. This facilitates installation and removal of the link arm. Fastened in lower link arm flange 85 and extending from its face is a shouldered guide pin 86' which is sized in diameter to fit into radially open slot 64 in the flange 62 on which torque shaft 59 for the X-ray casing cradle is fastened. Guide pin 86' cooperates with headed pin 86 to provide positive drive when flanges 62 and 85 are clamped together.

Although the means for clamping the link arm 40 to the tube cradle and intensifier shafts using flanges and pins has been described in detail, those skilled in the art will realize that any suitable releasable clamping means could be used.

As explained earlier, the X-ray tube can be used for conventional radiography and arteriography. In the conventional vertical radiography mode, the X-ray image intensifier assembly 21 and tube casing 36 are locked against angulation such that the central X-ray beam is coincident with the center of the image plane in the image intensifier. In this mode, the patient is shifted longitudinally and laterally with the patient supporting table 11 to place the anatomical region of interest in the central X-ray beam. Link arm 40 is preferably removed to allow greater access to the patient around the table in this mode.

For doing coronary artery examinations link arm 40 must be in place for transmitting the angulating force from intensifier assembly 21 to the X-ray tube cradle 58. To install link arm 40, the operator extends the telescoping link arm to substantially its final length. Shank 78 of the upper pin 77 is then dropped into slot 53 in flange 52 and is retained there by head 77 on the shank. Guide pin 78' enters slot 54 at the same time. Inner telescoping section 77 is then urged downwardly manually to enable shank 86 of the lower pin to enter slot 63 and guide pin 86' to enter slot 64 of flange 62 which is attached to shaft extension 59. Prior to the lower end being engaged, the operator may turn upper knob 76 to start thread 73 into threaded hole 55 in flange 52. Likewise, after shank 86 of the lower end is dropped into slot 63 in extension shaft flange 62, lower knob 83 is turned to cause engagement of thread 82 of the rod in the central hole 65 in flange 62. Both knobs 76 and 83 are then turned until the interfaced flanges on link arm 40 and the tube cradle and intensifier shafts are in firm contact.

Link arm 40 may be removed by simply backing the threads 73 and 82 of the upper and lower clamping rods out of the center holes 55 and 65 of their mating flanges. The arm 40 will remain in place during this operation due to the heads 77 and 87 on the upper and lower pins 78 and 86', respectively. Finally, link arm 40 is lifted slightly so that the heads 77 and 87 clear the slots in the flanges and the arm may be withdrawn. The link arm may then be telescoped to make it as short as possible before it is set aside or stored.

FIG. 3 also shows detent means for temporarily holding telescoping link arm 40 in a contracted condition when not in use. The detent means comprise a spring member 90 which has a V-shaped end 91 for engaging a hole 92 in outer tubular member 66. A mild endwise thrust in one direction on inner tubular member 67 is adequate to relieve the detent and permit extension of link arm 40 and a mild thrust in the other direction engages it.

For the use in the arteriographic mode with the link arm 40 clamped in place the apparatus functions as follows. Initially, the image intensifier assembly 21 is centered over the patient supporting table on a vertical line that runs through the focal spot 37 of the X-ray tube. If the examiner desires to take a view through the patient's heart at an angle to visualize a part of the coronary artery system that would otherwise be under another part or otherwise covered by confusing tissue, or to place some of the multidirectional coronary arteries in a plane that is perpendicular to the X-ray beam, the intensifier and tube casing are unlocked so the image intensifier and tube casing 36 may angulate jointly. Angulation is achieved by shifting intensifier assembly 21 horizontally such as by pushing in the longitudinal direction on telescoping support arm 32 or otherwise moving crane 30 longitudinally. This angulates the link arm 40 and the intensifier assembly 21 and turns the X-ray source cradle 58. Since the axis of rotation for the tube cradle 58 cannot shift laterally, it must angulate coordinately synchronously with the image intensifier assembly 21. In FIG. 2 image intensifier 21 is shown in phantom lines to illustrate attainment of one of its possible longitudinal angulations.

Angulation, of course, causes vertical extension of telescoping support 32 in which case the image intensifier assembly moves toward the patient who is supported on table 11. The design is such that the image intensifier assembly cannot be moved into contact with the patient. As a final step the examiner will move the image intensifier assembly 21 up or down by means of telescoping support 32 to achieve the desired X-ray tube focal spot-to-image distance for covering the anatomical area of interest. Regardless of the angle to which the image intensifier assembly 21 is tilted, the central beam from the X-ray tube focal spot always remains perpendicular to the image plane of the intensifier and in parallelism with link arm 40. The link arm assures that the intensifier assembly 21 and X-ray tube casing 36 always angulate by the same amount so as to maintain perpendicularity between the central X-ray beam and image plane. Conventional locking means, not heretofore discussed or shown are, of course, provided for selectively locking the crane 30 against longitudinal movement and telescoping arm 33 against vertical movement after the intensifier 21 and tube are angulated to the desired position and the desired focal spot-to-image plane distance has been set. Attainment of the desired angle and distance is determined conventionally by the examiner viewing the intensifier output image on a television monitor. In some installations there are fixed rails disposed over the X-ray table in a longitudinal direction, rather than transverse to the table as is bridge 40, in which case it is only necessary to have means for locking the telescoping arm 32 to the rails after the intensifier is angulated or when it is desired to center it with the table and remove the link arm 40.

It is significant that the image intensifier assembly 21 may be angulated on its open sided L-shaped cantilever arm 41 through the full angular range required for coronary arteriography without any interferences between the side mounted optical tunnel 25, camera 24 and cine camera 27 and either of the telescoping support arm 32 and the cantilever arm 41. Thus, supporting the image intensifier assembly 21 including the image recording cameras 24 and 27 in cantilever fashion on arm 41 is an important feature of the X-ray diagnostic system.

We claim:

1. X-ray apparatus characterized by being adaptable to conduct general body examinations and coronary arteriographic examinations, comprising:
   a support means that is extensible and contractible vertically and means on which said support means is mounted for movement in opposite longitudinal directions,
   an arm means having first and second parts arranged at an angle to each other, the first part being attached to said support means and extending in cantilever fashion therefrom,
   an image intensifier assembly disposed adjacent said parts within the angle defined thereby,
   first shaft means journalled on said second arm part, said image intensifier assembly being carried on said shaft means,
   X-ray source means disposed below said intensifier assembly and in substantial spaced relationship for accommodating an examination subject between them,
   second shaft means on which said X-ray source means is carried, the axes of said first and second shaft means being laterally directed and parallel to each other,
   means on which said second shaft means is supported and journalled,
   extensible and contractible link arm means having opposed ends each of which has means for rigidly clamping to said shaft means, respectively, and for being released therefrom selectively, longitudinal movement of said cantilever arm means when said link arm means is clamped causing said link arm means to angulate and effect coordinate angulation and constant alignment of said image intensifier system and said X-ray source.

2. The apparatus in claim 1 including:
   pairs of cooperating mating members, one of which members in each pair is fastened to a shaft means and the other member in the pair is fastened to said link arm means,
   one member in each pair having a slot and the other having a protruding pin for engaging in said slot to facilitate installing said link arm means.

3. The apparatus in claim 2 wherein one of each member in a pair has thread means, manually turnable rod means for each respective pair, said rod means being carried in said link arm means and having cooperating thread means and being turnable to clamp said members together.

4. The apparatus in claim 2 wherein said pin means have heads for retaining them in said members during the procedure for installing and removing said link arm means.

5. The apparatus in claim 1 wherein said link arm means comprises telescoping sections for permitting said extension and contraction.

6. Diagnostic X-ray apparatus comprising:
   X-ray source means and an X-ray image intensifier assembly in spaced apart relationship for disposing an X-ray examination subject between them,
   support means constructed and arranged for performing at least generally horizontal movements,
   arm means connected to said support means and extending in cantilever fashion therefrom,
   first shaft means journalled for rotation on said arm means at a place that is spaced from where said arm means is connected to said support means, said image intensifier assembly being connected to said shaft means,
   second shaft means and means journaling said means for rotation about an axis that is parallel with the axis of said first shaft means, said X-ray source means being connected to said second shaft means,
   link arm means including means for selectively engaging said link arm means rigidly to said first and second shaft means, such that when said support means is moved horizontally said link arm means will turn and cause said intensifier assembly and said X-ray source means to rotate through the same angle.

7. The apparatus of claim 6 wherein said arm means has two portions arranged in a substantially L-shape and one end thereof is connected to said support means and said first shaft means is journalled in another end thereof, said intensifier assembly being disposed on the inside of said L-shaped arm means.

8. The apparatus of claim 7 including image recording devices on at least two of the sides of said image intensifier assembly.

9. The apparatus of claim 7 including a spot film camera on one side of said image intensifier assembly and a cine recording camera on another side thereof.

10. The apparatus of claim 6 characterized as a three-port system having a camera mounted on each of at least two sides of said image intensifier system and a television camera in the upper portion thereof.

11. The apparatus of claim 6 in which said support means is constructed and arranged for also performing generally vertical movements.

12. The apparatus of claim 6 including a slotted member attached to each of said shaft means, opposite ends of said link arm means each having pin means for entering said slot means, and means at each of said link arm means for clamping it to said members, respectively.

13. The apparatus in claim 6 wherein said link arm means is extensible and contractible.

14. The apparatus in claim 6 wherein said support means comprises crane means, a vertically disposed extensible and contractible arm means mounted to said crane means, said first shaft means being supported by said arm means.

15. The apparatus in claim 6 wherein said support means comprises crane means, a vertically disposed extensible and contractible arm means mounted to said crane means, said arm means which extends in cantilever fashion having a first portion fastened to said extensible and contractible arm means and a second portion extending in cantilever fashion away from said first portion, said first shaft means being journalled in said second portion.

16. The apparatus in claim 6 wherein said link arm means comprises arm sections that are joined for movement relative to each other to permit distance changes between said first and second shaft means.

* * * * *